US012514773B2

(12) United States Patent
Park

(10) Patent No.: US 12,514,773 B2
(45) Date of Patent: Jan. 6, 2026

(54) MEDICAL DEVICE FOR RELAXING SPINE

(71) Applicant: Jang Hyung Park, Ulsan (KR)

(72) Inventor: Jang Hyung Park, Ulsan (KR)

( * ) Notice: Subject to any disclaimer, the term of this patent is extended or adjusted under 35 U.S.C. 154(b) by 274 days.

(21) Appl. No.: 18/317,520

(22) Filed: May 15, 2023

(65) Prior Publication Data

US 2023/0363934 A1 Nov. 16, 2023

(30) Foreign Application Priority Data

May 16, 2022 (KR) ........................ 10-2022-0059319

(51) Int. Cl.
*A61H 1/02* (2006.01)
*A61F 5/02* (2006.01)

(52) U.S. Cl.
CPC ............. *A61H 1/0292* (2013.01); *A61F 5/02* (2013.01); *A61H 2201/0149* (2013.01); *A61H 2201/1638* (2013.01)

(58) Field of Classification Search
CPC ...... A61H 1/02; A61H 1/0214; A61H 1/0218; A61H 1/0222; A61H 1/0229; A61H 1/0292; A61H 2001/0233; A61F 5/02; A61F 5/026; A61F 5/028; A61F 5/03; A61F 5/04; A61F 5/042; A61F 5/048; A61F 5/3769; A61F 5/3776; A61F 5/3784; A61F 5/3792; A61G 5/12; A61G 5/14; A61G 5/122;

(Continued)

(56) References Cited

U.S. PATENT DOCUMENTS 1,722,205 A * 7/1929 Freund .................... A61F 5/024 602/19
3,063,752 A * 11/1962 Moore ................. A61H 1/0292 5/81.1 R (Continued)

FOREIGN PATENT DOCUMENTS

AT 998 * 12/1995 ............ A63B 23/02
CN 202950801 U 5/2013

(Continued)

OTHER PUBLICATIONS

Request for Submission of Opinion dated Jul. 13, 2022 for corresponding KR Application 10-2022-0059319 and English translation thereof.

(Continued)

*Primary Examiner* — Adam Baker
(74) *Attorney, Agent, or Firm* — Tarolli, Sundheim, Covell & Tummino LLP

(57) ABSTRACT

Proposed is a medical device for relaxing the spine that is easy to move and keep and can be easily used in real life. The medical device for relaxing the spine include a chair having a seat and a back, a first armpit support disposed at a left side of the chair, and a second armpit support disposed at a right side of the chair, in which the first armpit support and the second armpit support each include a cylinder vertically coupled to the chair, a first spring disposed in the cylinder and configured to protrude upward out of the cylinder when being rotated in one direction, a second spring coupled to an upper end of the first spring and having a spring constant smaller than a spring constant of the first spring, a bar disposed over the second spring and configured to come in close contact with an armpit.

3 Claims, 5 Drawing Sheets

(58) Field of Classification Search
CPC ........ A61G 5/124; A61G 5/125; A47C 7/425; A47C 7/54; A47C 1/03; A63B 23/02; B60N 2/64; B60N 2/643; B60N 2/646
USPC ........................................................... 602/19
See application file for complete search history.

(56) References Cited

U.S. PATENT DOCUMENTS

| | | | | | |
|---|---|---|---|---|---|
| 3,548,817 | A * | 12/1970 | Mittasch | ................. | A61F 5/024<br>602/19 |
| 5,462,518 | A | 10/1995 | Hatley et al. | | |
| 2005/0245854 | A1 | 11/2005 | Leuthardt et al. | | |
| 2009/0146475 | A1* | 6/2009 | Rutty | ..................... | A47C 7/425<br>297/230.1 |
| 2016/0058597 | A1* | 3/2016 | Williams | ................ | A61F 5/028<br>602/19 |
| 2018/0360641 | A1 | 12/2018 | Budge | | |
| 2019/0091056 | A1* | 3/2019 | Lee | ........................... | A61F 5/02 |

FOREIGN PATENT DOCUMENTS

| | | | | | |
|---|---|---|---|---|---|
| CN | 103284865 | | 9/2013 | | |
| CN | 106109067 | A | 11/2016 | | |
| DE | 202013001227 | * | 5/2013 | ............... | A61F 5/02 |
| JP | 60-044651 | U | 3/1985 | | |
| JP | 2006180972 | A | 7/2006 | | |
| KR | 10-1481811 | | 1/2015 | | |
| KR | 10-2016-0125825 | | 11/2016 | | |
| KR | 20-0176863 | | 4/2020 | | |
| KR | 20210055029 | A | 5/2021 | | |

OTHER PUBLICATIONS

Decision of Rejection dated Oct. 25, 2022 for corresponding KR Application 10-2022-0059319 and English translation thereof.
Decision to Grant dated Apr. 21, 2023 for corresponding KR Application 10-2022-0059319 and English translation thereof.
The Extended European Search Report dated Oct. 2, 2023 in the corresponding European Application No. 23172509.4.
The Notice of Allowance in the corresponding Japanese Application No. 2023-076354.

* cited by examiner

[FIG. 1]
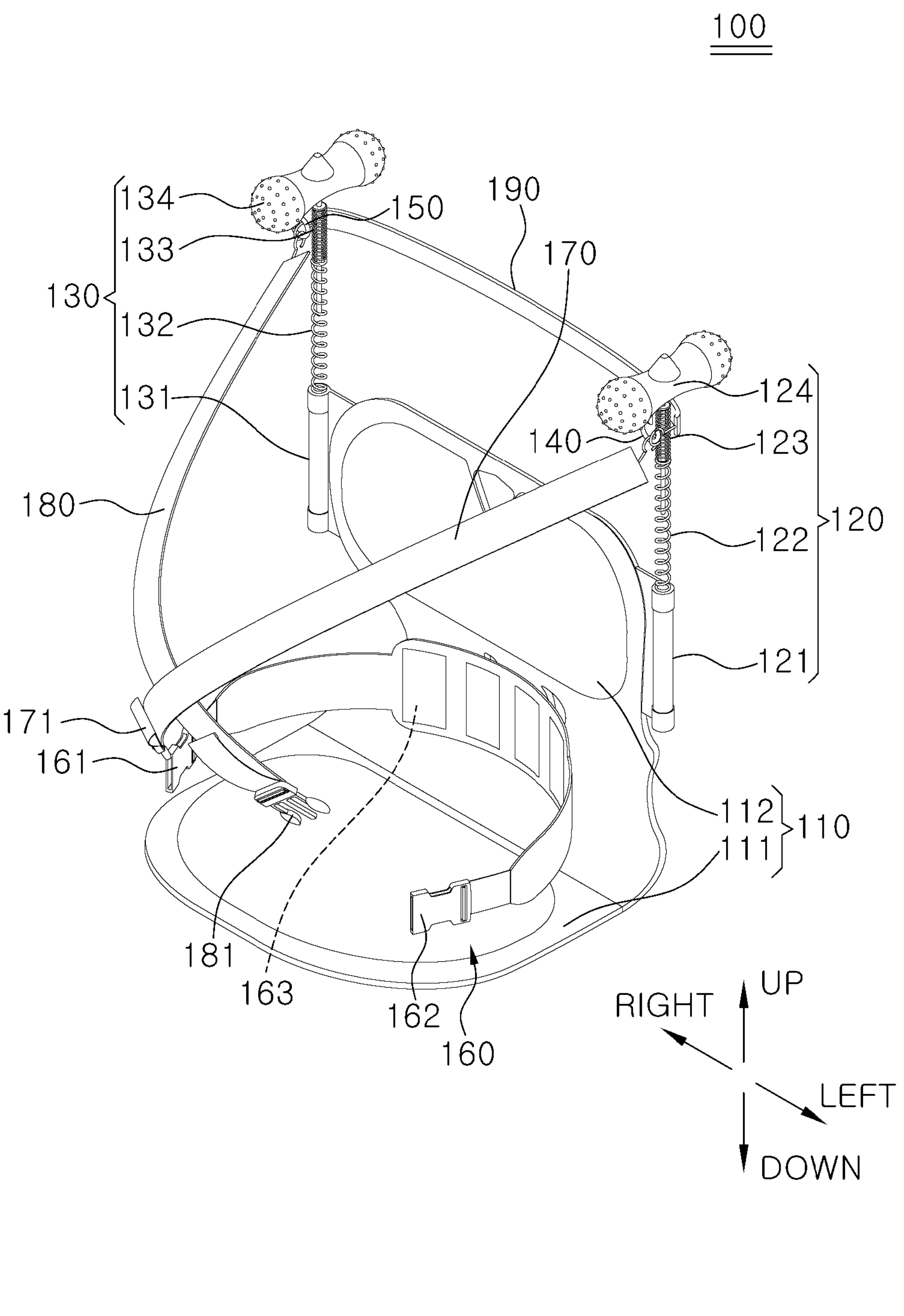

[FIG. 2]
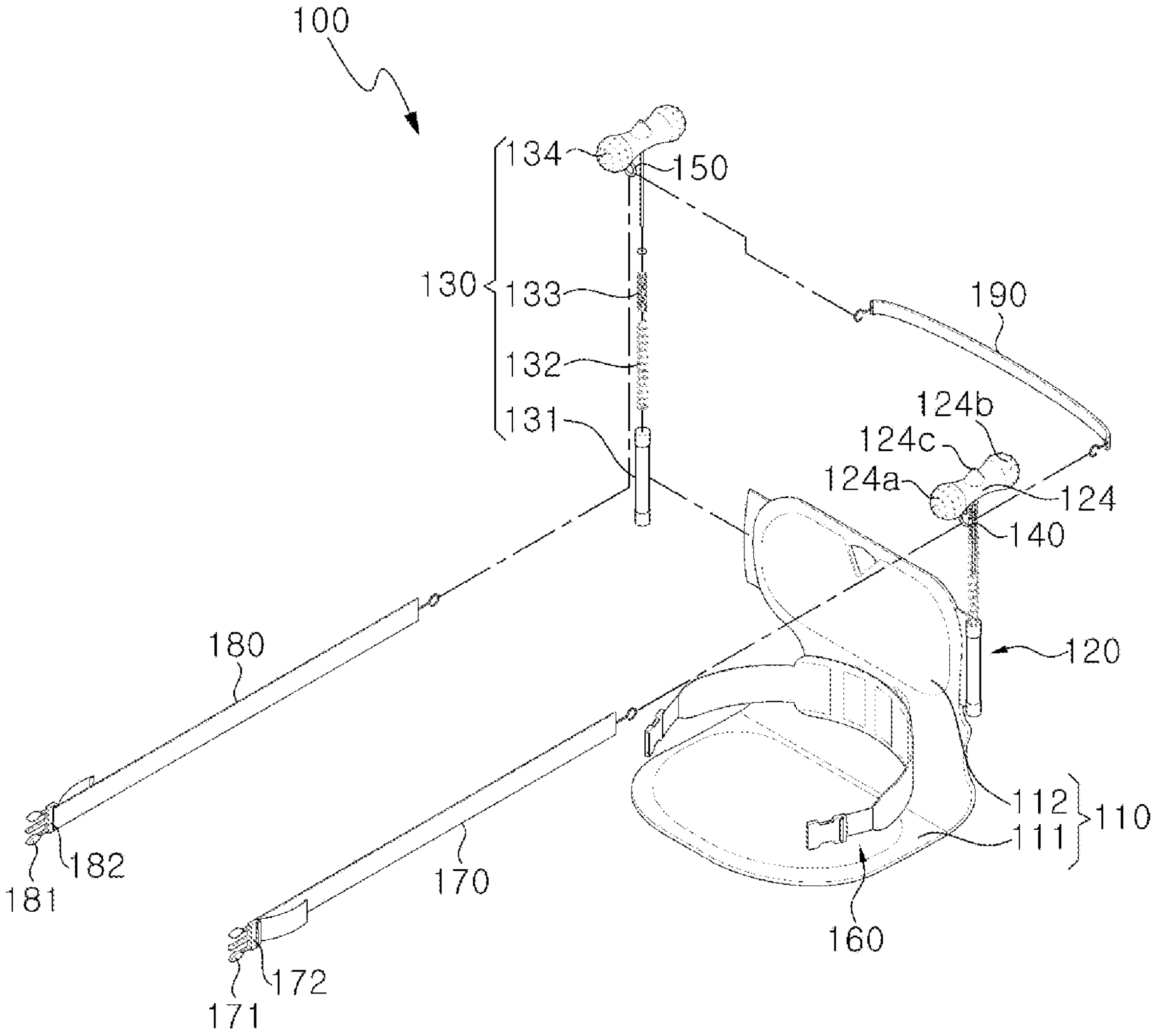

[FIG. 3]
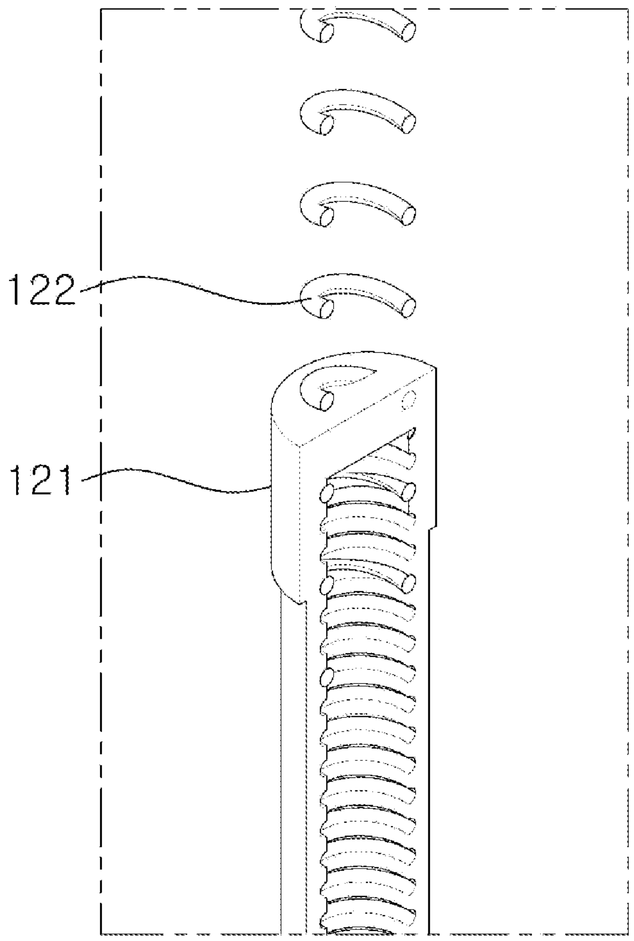

[FIG. 4]
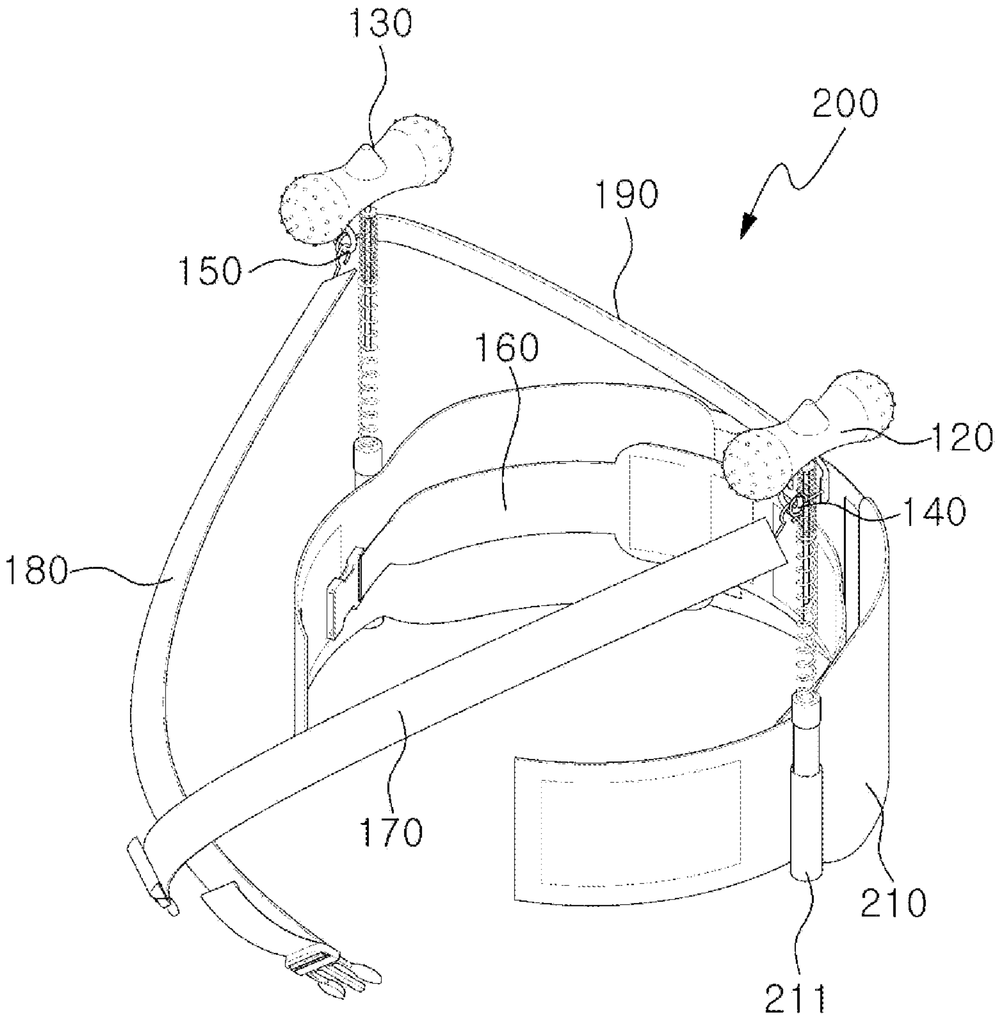

[FIG. 5]
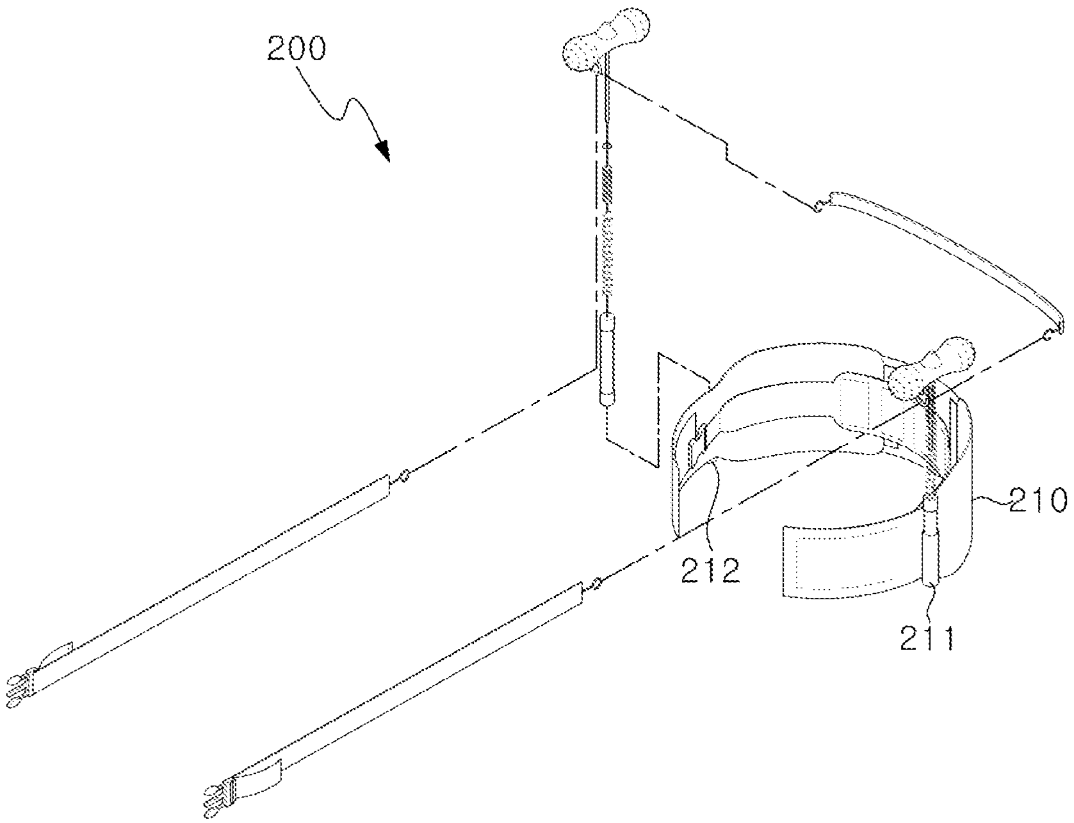

MEDICAL DEVICE FOR RELAXING SPINE

CROSS REFERENCE TO RELATED APPLICATION

The present application claims priority to Korean Patent Application No. 10-2022-0059319, filed May 16, 2022, the entire contents of which are incorporated herein for all purposes by this reference.

BACKGROUND OF THE INVENTION

Field of the Invention

The present disclosure relates to a medical device that reduces a load, which is applied to the spine, by relaxing the spine.

Description of the Related Art

An example of a medical device that reduces a load, which is applied to the spine, by relaxing the spine has been disclosed in Korean Utility Model No. 20-0176863 (published on Apr. 15, 2000).

The spine relaxing device for health (hereafter, referred to as a "medical device for relaxing the spine in the related art") includes two parallel erect guide columns, a geared motor that is switched on to generate power by rotating forward or backward, a power transmission unit that is operated by power from the geared motor to transmit a rotation force, a first sprocket that is rotatably installed at the lower end inside each of the guide columns and is rotated by the power transmission unit, a second sprocket that is rotatably installed at the upper end inside each of the guide columns, a chain that is installed between the first sprockets and the second sprockets and links the first sprockets and the second sprockets, a bed that has an upper end rotatably installed at a side of the chain, has a roller installed at a lower end thereof, and is inclined by operation of the chain, and an ankle holder that is installed and fixed at the upper end of the bed and fixes the ankle of a person.

Meanwhile, the medical device for relaxing the spine in the related art is not easy to move and keep due to the size and weight. Further, it is required to separately spare time in order to use the medical device for relaxing the spine in the related art.

SUMMARY OF THE INVENTION

An objective of the present disclosure is to provide a medical device for relaxing the spine that is easy to move and keep and can be easily used in real life.

Medical devices for relaxing the spine according to embodiment(s) of the present disclosure are described.

A medical device for relaxing the spine according to a first embodiment includes: a chair having a seat and a back; a first armpit support disposed at a left side of the chair; and a second armpit support disposed at a right side of the chair, in which the first armpit support and the second armpit support each include: a cylinder vertically coupled to the chair; a first spring disposed in the cylinder and configured to protrude upward out of the cylinder when being rotated in one direction; a second spring coupled to an upper end of the first spring and having a spring constant smaller than a spring constant of the first spring; and a bar disposed over the second spring and configured to come in close contact with an armpit.

The medical device for relaxing the spine according to the first embodiment may further include: a first ring disposed at an upper portion of the first armpit support; a second ring disposed at an upper portion of the second armpit support; an elastic waist band configured to be wrapped around the waist of a user, having a first female buckle at a right end thereof, and a second female buckle at a left end thereof; a first chest band having a first end configured to be fastened to the first ring and having a first male buckle configured to be fastened to the first female buckle at a second end thereof; a second chest band having a second end configured to be fastened to the second ring and having a second male buckle configured to be fastened to the second female buckle at a second end thereof; and an elastic connection band configured to connect the first ring and the second ring to each other.

In some embodiments, the medical device for relaxing the spine may further include a rod inserted inside the second spring and disposed under the bar.

A medical device for relaxing the spine according to a second embodiment includes: a waist protector; a first armpit support disposed at a left side of the waist protector; and a second armpit support disposed at a right side of waist protector, in which the first armpit support and the second armpit support each include: a cylinder vertically coupled to the waist protector; a first spring disposed in the cylinder and configured to protrude upward out of the cylinder when being rotated in one direction; a second spring coupled to an upper end of the first spring and having a spring constant smaller than a spring constant of the first spring; and a bar disposed over the second spring and configured to come in close contact with an armpit.

The medical device for relaxing the spine according to the second embodiment may include: a first ring disposed at an upper portion of the first armpit support; a second ring disposed at an upper portion of the second armpit support; an elastic waist band configured to be wrapped around the waist of a user, having a first female buckle at a right end thereof, and a second female buckle at a left end thereof; a first chest band having a first end configured to be fastened to the first ring and having a first male buckle configured to be fastened to the first female buckle at a second end thereof; a second chest band having a second end configured to be fastened to the second ring and having a second male buckle configured to be fastened to the second female buckle at a second end thereof; and an elastic connection band configured to connect the first ring and the second ring to each other.

In some embodiments, the medical device for relaxing the spine may further include a rod inserted inside the second spring and disposed under the bar.

The medical devices for relaxing the spine according to various embodiments described above have an effect of reducing a load that is applied to the spine by relaxing the spine and of correcting the posture of a user.

Further, the medical devices for relaxing the spine according to various embodiments are configured in a chair type (or a waist protector type), so they are easy to move and keep and can be used in real life.

BRIEF DESCRIPTION OF THE DRAWINGS

The above and other objectives, features and other advantages of the present invention will be more clearly understood from the following detailed description when taken in conjunction with the accompanying drawings, in which:

FIG. 1 is a perspective view of a medical instrument for relaxing the spine according to a first embodiment;

FIG. 2 is an exploded perspective view of the medical instrument for relaxing the spine according to the first embodiment;

FIG. 3 is a cross-sectional view showing the operation relationship between a cylinder and a first spring;

FIG. 4 is a perspective view of a medical instrument for relaxing the spine according to a second embodiment; and FIG. 5 is an exploded perspective view of the medical instrument for relaxing the spine according to the second embodiment.

DETAILED DESCRIPTION OF THE INVENTION

Hereafter, medical instruments for relaxing the spine according to various embodiments are described in detail with reference to the accompanying drawings.

FIG. 1 is a perspective view of a medical device 100 for relaxing the spine according to a first embodiment (hereafter, referred to as a "medical device 100 for relaxing the spine") and FIG. 2 is an exploded perspective view of the medical device 100 for relaxing the spine.

As shown in FIGS. 1 and 2, the medical device 100 for relaxing the spine includes a chair 110, a first armpit support 120, and a second armpit support 130.

The expressions representing directions of components (defining directions) ("front", "rear", "left(side)", "right (side)", etc.) are based on FIG. 1.

The chair 110 includes a seat 111 supporting the user's hips and a back 112 supporting the user's back. The chair 110 may be made of a synthetic resin material, a wood material, a metal material, etc. The seat 111 and the back 112 may be made of different materials.

The first armpit support 120 has a predetermined length, is coupled to the left side of the chair 110, and supports the left armpit of a user.

The second armpit support 130 has a predetermined length, is coupled to the right side of the chair 110, and supports the right armpit of a user.

The first armpit support 120 and the second armpit support 130 may be coupled to the back 112, as shown in figures, or, though not shown in figures, may be coupled to the seat 111, depending on intention of manufacturers.

The first armpit support 120 and the second armpit support 130 may be configured in the same size and shape. In this case, the first armpit support 120 and the second armpit support 130 may be switched.

The first armpit support 120 may be composed of a cylinder 121, a first spring 122, a second spring 123, and a bar 124.

The cylinder 121 has a predetermined length. The cylinder 121 may be coupled to the back 112. The cylinder 121 is perpendicular to the ground.

The first spring 122 has a predetermined length and is disposed in the cylinder 121. The first spring 122 is configured to protrude upward out of the cylinder 122 when it is rotated in one direction. That is, the height of the first spring 122 can be adjusted with respect to the cylinder 121. As a detailed example, as shown in FIG. 3, the diameter of the first spring 122 may correspond to the inner diameter of the cylinder 121 and corrugations may be diagonally formed inside the cylinder 121. The first spring 122 may be bend forward, rearward, left, and right by movement of the user's upper body.

Referring to FIGS. 1 and 2 again, the second spring 123 is disposed over the first spring 122. The second spring 123 has a length smaller than that of the first spring 122. The spring constant of the second spring is smaller than the spring constant of the first spring 122. In detail, the first spring 122 has a spring constant that is enough not to be vertically compressed by the weight of a user and the second spring 123 has a spring constant that is enough to be easily vertically compressed by the weight of a user. That is, the first spring 122 stably supports the upper body of a user and the second spring 123 serves to fill the space between an armpit and the first spring 122 without discomfort.

The bar 124 is disposed over the second spring 123. The bar 124 may have an arc shape when seen from a side. The bar 123 is designed to be brought in close contact with an armpit of a user. The entire or the surface of the bar 124 may be made of a cushioning material.

Pressing sections 124*a*, 124*b*, and 124*c* may protrude at the front end, the rear end, and the upper portion of the middle.

Referring to FIG. 3, the bar 124 may be configured to be detachably coupled to the second spring 123. For example, the bar 124 may have a rod on the bottom that is inserted inside the second spring 123 and a ring plate may be disposed on the second spring 123.

The rod may have a length slightly larger than that of the second spring 123. The rod prevents front-rear and left-right deformation of the second spring 123 due to movement of the user's upper body.

The second armpit support 130, the same as the first armpit support 120, may be composed of a cylinder 131, a first spring 132, a second spring 133, and a bar 134.

The medical device 100 for relaxing the spine may further include a first ring 140, a second ring 150, an elastic waist band 160, a first chest band 170, a second chest band 180, and an elastic connection band 190.

The first ring 140 is disposed at the upper portion of the first armpit support 120. In detail, the first ring 140 may be disposed under the bar 124. The first ring 140 may be integrated with the bar 124.

The second ring 150 is disposed at the upper portion of the second armpit support 130. In detail, the second ring 150 may be disposed under the bar 134. The second ring 150 may be integrated with the bar 134.

The elastic waist band 160 has a predetermined length and is configured to be wrapped around the waist of a user. The elastic waist band 160 is made of an elastic material such as rubber and latex and supporting members that have predetermined rigidity and supporting a waist may be disposed in the elastic waist band 160.

A first female buckle 161 is disposed at the right end of the elastic waist band 160 and a second female buckle 162 is disposed at the left end of the elastic waist band 160. The first female buckle 161 and the second female buckle 162 may have the same specifications.

A first end of the first chest band 170 is fastened to the first ring 140 and a first male buckle 171 that is fastened to the first female buckle 161 is disposed at a second end of the first chest band 170. That is, the first chest band 170 is designed to go to the right side of the user's waist across the left chest from the left armpit of the user.

The first chest band 170 may further have a length adjuster 172, so the length thereof can be adjusted.

A first end of the second chest band 180 is fastened to the second ring 150 and a second male buckle 181 that is fastened to the second female buckle 162 is disposed at a second end of the second chest band 180. That is, the second chest band 180 is designed to go to the left side of the user's waist across the right chest from the right armpit of the user.

The second chest band 180 may further have a length adjuster 182, so the length thereof can be adjusted.

The first chest band 170 and the second chest band 180 may have the same specifications.

The elastic waist band 160, the first chest band 170, and the second chest band 180 press forward the waist (the lumbar vertebra) of a user sitting on the chair 110 such that the user's spine is maintained in an "S" shape, and the first armpit support 140 and the second armpit support 150 are brought in close contact with the trunk of the user.

The elastic connection band 180 is made of an elastic material such as rubber and latex, directly connects the first ring 140 and the second ring 150, and is positioned behind the upper portion of the back of a user. The elastic connection band 190 serves to pull the first armpit support 120 and the second armpit support 130 toward the trunk of a user.

FIG. 4 is a perspective view of a medical device 200 for relaxing the spine according to a second embodiment (hereafter, referred to as a "medical device 200 for relaxing the spine") and FIG. 5 is an exploded perspective view of the medical device 200 for relaxing the spine.

Referring to FIGS. 4 and 5, the chair 110 of the medical device 100 for relaxing the spine may be replaced with a waist protector 210. The waist protector 210 has a band shape and may be configured such that both ends thereof are fastened to each other through buckles, Velcro, a zipper, or the like. Pockets 211 that receive the lower portions of the first armpit support 120 and the second armpit support 130 may be disposed on the outer surface of the waist protector 210, and the first armpit support 120 and the second armpit support 130 may be configured to be detachably coupled to the waist protector 210.

The elastic waist band 160 may be disposed at any position regardless of the inside or the outside of the waist protector 210, depending on the user's taste.

The medical devices 100 and 200 for relaxing the spine according to various embodiments described above have an effect of reducing a load that is applied to the spine by relaxing the spine and of correcting the posture of a user.

Further, the medical devices 100 and 200 for relaxing the spine according to various embodiments are configured in a chair type (or a waist protector type), so they are easy to move and keep and can be used in real life.

What is claimed is:

1. A medical device for relaxing a spine, comprising:

a chair having a seat and a back;

a first armpit support disposed at a left side of the chair; and a second armpit support disposed at a right side of the chair, wherein the first armpit support and the second armpit support each include:

a cylinder vertically coupled to the chair;

a first spring disposed in the cylinder and configured to protrude upward out of the cylinder when being rotated in one direction;

a second spring coupled to an upper end of the first spring and having a spring constant smaller than a spring constant of the first spring;

a bar disposed over the second spring and configured to come in close contact with an armpit; and a rod having a length larger than a length of the second spring, disposed under the bar, inserted inside the second spring, and configured to prevent front-rear and left-right deformation of the second spring.

2. The medical device for relaxing a spine of claim 1, further comprising:

a first ring disposed at an upper portion of the first armpit support;

a second ring disposed at an upper portion of the second armpit support;

an elastic waist band configured to be wrapped around the waist of a user, having a first female buckle at a right end thereof, and a second female buckle at a left end thereof;

a first chest band having a first end configured to be fastened to the first ring and having a first male buckle configured to be fastened to the first female buckle at a second end thereof; and a second chest band having a first end configured to be fastened to the second ring and having a second male buckle configured to be fastened to the second female buckle at a second end thereof.

3. The medical device for relaxing a spine of claim 2, further comprising an elastic connection band configured to connect the first ring and the second ring to each other.

* * * * *